US010634661B2

(12) United States Patent
Ishizaka et al.

(10) Patent No.: US 10,634,661 B2
(45) Date of Patent: Apr. 28, 2020

(54) BLOOD ANALYSIS METHOD AND BLOOD TEST KIT

(71) Applicant: FUJIFILM Corporation, Tokyo (JP)

(72) Inventors: Tatsuya Ishizaka, Ashigarakami-gun (JP); Haruyasu Nakatsugawa, Ashigarakami-gun (JP); Susumu Osawa, Tokyo (JP); Shinya Sugimoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 155 days.

(21) Appl. No.: 15/861,209

(22) Filed: Jan. 3, 2018

(65) Prior Publication Data

US 2018/0128807 A1 May 10, 2018

Related U.S. Application Data

(63) Continuation of application No. PCT/JP2016/070010, filed on Jul. 6, 2016.

(30) Foreign Application Priority Data

Jul. 6, 2015 (JP) .................................. 2015-135064
Jul. 6, 2016 (JP) .................................. 2016-133960

(51) Int. Cl.
*G01N 33/49* (2006.01)
*G01N 33/48* (2006.01)
(Continued)

(52) U.S. Cl.
CPC ....... *G01N 33/49* (2013.01); *A61B 5/150022* (2013.01); *A61B 5/150343* (2013.01);
(Continued)

(58) Field of Classification Search
CPC .... G01N 33/49; G01N 33/487; G01N 33/483; G01N 33/48; A61B 5/150022; A61B 5/0015; A61B 5/0007; A61B 5/15
(Continued)

(56) References Cited

U.S. PATENT DOCUMENTS 5,001,067 A 3/1991 Coleman et al.
2001/0055784 A1 12/2001 Noda et al.
(Continued)

FOREIGN PATENT DOCUMENTS

CN 101185001 A 5/2008
JP 2001-330603 A 11/2001
(Continued)

OTHER PUBLICATIONS

Kyowa Medex Co., Ltd, WO 03/005039 A1, English Machine Translation, obtain by STIC at the USPTO, obtained on Jul. 29, 2019, pp. 1-69. (Year: 2019).*
(Continued)

*Primary Examiner* — Christine T Mui
(74) *Attorney, Agent, or Firm* — Sughrue Mion, PLLC (57) ABSTRACT

An object of the present invention is to provide a blood analysis method in which a high level of repeatability and reproducibility is achieved with respect to measurement values in a blood sample of 50 μL or less, and a blood test kit which is used for the blood analysis method. According to the present invention, a blood analysis method including a step of diluting a collected blood sample with a diluent solution; a step of determining a dilution factor by using a normal value of a normal component which is homeostatically present in the blood; and a step of analyzing a concentration of a target component in the blood sample, in which a volume of the blood sample is 50 μL or less, a dilution factor of blood plasma components in the blood
(Continued)

sample is 14 or higher, and the diluent solution is a diluent solution which does not contain the normal component which is homeostatically present in the blood, is provided.

14 Claims, 1 Drawing Sheet

(51) Int. Cl.
| | |
|---|---|
| *A61B 5/15* | (2006.01) |
| *G01N 33/96* | (2006.01) |
| *G01N 33/84* | (2006.01) |
| *G01N 1/10* | (2006.01) |
| G01N 1/38 | (2006.01) |
| G01N 33/66 | (2006.01) |

(52) U.S. Cl.
CPC ......... *A61B 5/150755* (2013.01); *G01N 1/10* (2013.01); *G01N 33/48* (2013.01); *G01N 33/491* (2013.01); *G01N 33/84* (2013.01); *G01N 33/96* (2013.01); *A61B 5/150206* (2013.01); *A61B 5/150351* (2013.01); *G01N 1/38* (2013.01); *G01N 33/66* (2013.01); *G01N 2333/765* (2013.01)

(58) Field of Classification Search
USPC .......................................................... 436/10
See application file for complete search history.

(56) References Cited

U.S. PATENT DOCUMENTS

| | | | |
|---|---|---|---|
| 2002/0153316 A1 | 10/2002 | Nanba et al. | |
| 2005/0232813 A1 | 10/2005 | Karmali | |
| 2011/0020195 A1* | 1/2011 | Luotola .............. | A61B 10/0045 422/512 |
| 2016/0011150 A1* | 1/2016 | Onuma ............ | G01N 27/44791 204/451 |

FOREIGN PATENT DOCUMENTS

| | | | | |
|---|---|---|---|---|
| JP | 2003-161729 A | | 6/2003 | |
| JP | 2009-109196 A | | 5/2009 | |
| JP | 2009-122082 A | | 6/2009 | |
| JP | 2011-112451 A | | 6/2011 | |
| JP | 2014-141829 | * | 7/2014 | .......... G01N 27/447 |
| JP | 2015-105936 A | | 6/2015 | |
| WO | WO 03/005039 A1 | * | 1/2003 | ............ G01N 33/72 |
| WO | 2011/065212 A1 | | 6/2011 | |

OTHER PUBLICATIONS

Office Action dated Mar. 15, 2019 from the State Intellectual Property Office of People's Republic of China in counterpart Chinese application No. 201680039333.2.
Extended European Search Report (EESR) dated Jun. 6, 2018 from the European Patent Office in counterpart European application No. 16821434.4.
Horita, M., et al., "Establishment of Mail Medical Examination System Using Immediate Plasma Separating Device by the Self-Collection Blood: The Method of Dilution Ratio Calculation by Using Internal Standard for the Sample with Different Amount of Collecting Blood", Rinsho Byori/ Japanese Journal of Clinical Pathology, vol. 56, No. 7, Jul. 25, 2008, pp. 577-583, XP009503400.
Communication dated May 20, 2019 from the Korean Intellectual Property Office in counterpart Korean application No. 10-2018-7000464.
Susumu Osawa, et al., "Revolution of medical services at home using a small amount of blood collected from the fingertip", Journal of Clinical Laboratory Medicine, May 15, 2015, vol. 59, No. 5, pp. 397-404 (total 9 pages).
International Search Report for PCT/JP2016/070010 dated Oct. 4, 2016 [PCT/ISA/210].
Written Opinion of the International Searching Authority dated Oct. 4, 2016, in counterpart International Application No. PCT/JP2016/070010.
International Preliminary Report on Patentability dated Aug. 3, 2017, in counterpart International Application No. PCT/JP2016/070010.
Office Action dated Jul. 22, 2019, from the European Patent Office in European Application No. 16821434.4.

* cited by examiner

BLOOD ANALYSIS METHOD AND BLOOD TEST KIT

CROSS-REFERENCE TO RELATED APPLICATIONS

This application is a Continuation of PCT International Application No. PCT/JP2016/070010 filed on Jul. 6, 2016, which claims priority under 35 U.S.C § 119(a) to Japanese Patent Application No. 2015-135064 filed on Jul. 6, 2015 and Japanese Patent Application No. 2016-133960 filed on Jul. 6, 2016. Each of the above application(s) is hereby expressly incorporated by reference, in its entirety, into the present application.

BACKGROUND OF THE INVENTION

1. Field of the Invention

The present invention relates to a blood analysis method and a blood test kit for analyzing a target component in a small volume of a blood sample.

2. Description of the Related Art

As blood collection, generally, there are general blood collection in which a qualified person such as a doctor collects blood from the vein using a syringe, and self-blood collection in which a subject to be tested pricks his finger and the like using a blood collection needle so as to collect blood.

The blood collected by the general blood collection is transported to a medical institution or a test institution in a sealed state in a blood collection container, and tests are performed therein. In a case where the blood is transported without separating blood cells and blood plasma, tests are performed after a medical institution or a test institution performs centrifugation to separate the blood into blood cells and blood plasma. In addition, in the self-blood collection which is performed by a subject to be tested, the collected blood is separated into blood cells and blood plasma by a separation membrane, and the blood is transported to a test lab in a separated state, and then tests are performed therein.

JP2003-161729A discloses a method for testing a blood sample collected by self-blood collection, and specifically discloses a method for quantitatively determining a component to be quantitatively determined in a biological specimen, the method including 1) step of preparing a specimen for quantitation consisting of an unknown volume of a biological specimen containing a component to be quantitatively determined which is collected without quantitatively determining the volume thereof, and a certain volume of an aqueous solution containing a certain amount of an indicator substance, 2) step of obtaining a dilution factor (a) of the biological specimen from a concentration ($C_1$) of the indicator substance in the aqueous solution of a certain volume which contains a certain amount of the indicator substance, and a concentration ($C_2$) of the indicator substance in the specimen for quantitation, 3) step of obtaining a concentration (Y) of the component to be quantitatively determined in the specimen for quantitation, and 4) step of determining the component to be quantitatively determined in the biological specimen from the dilution factor (a) of the biological specimen obtained in 2), and the concentration (Y) of the substance to be quantitatively determined in the specimen for quantitation obtained in 3).

JP2001-330603A discloses a quantitative analysis method in which an amount of a target component to be analyzed in a sample is measured, an amount of a normal component originally and homeostatically present in the sample, other than the target component, is measured, a volume of the sample is determined from the amount of this normal component and a known concentration of the normal component in the sample, and therefore a concentration of the target component to be analyzed in the sample is determined from the volume of the sample and the amount of the target component to be analyzed.

In addition, JP2009-122082A discloses that a small volume of blood is collected from a human or an animal using a blood dilution quantitative instrument, and after dilution of the blood, or without dilution, a certain volume thereof is supplied to another instrument or container or is directly supplied to a reagent. Furthermore, JP2009-109196A discloses a method for quantitatively determining a concentration of a component to be quantitatively determined in a biological specimen by utilizing an absorbance of an indicator substance in an aqueous solution for dilution.

Meanwhile, in a case where a subject to be tested collects a blood sample, the blood is collected by using a lancet equipped with a small blade, and is used for quantitatively determining a concentration of an arbitrary component in the blood, but generally, it is required to collect 100 μL or more of a blood sample.

SUMMARY OF THE INVENTION

In the method disclosed in JP2003-161729A, it is required that a ratio of a diluent solution to a blood sample volume is set high in a case of a small volume of a blood sample. In this case, a change rate in a volume of a diluent solution before and after diluting the blood sample becomes very small, and a change rate in a concentration of an internal standard substance becomes small, and therefore there is a problem that a level of repeatability and reproducibility with respect to measurement values decreases.

JP2001-330603A discloses that about 100 μL of whole blood of a healthy subject is added dropwise to a porous membrane, blood cells are separated to develop serum, and thereafter, 150 μL of a physiologically isotonic solution, PBS (phosphate-buffered saline: pH 7.4) is added thereto, and the supernatant obtained by centrifuging the obtained solution is analyzed as an analytical specimen, but does not disclose collection of blood of less than 100 μL.

In the method of JP2009-122082A, a blood volume of 10 μL is accurately collected with a micropipette so as to be analyzed, but in a case where the blood is collected by a patient who lacks experience in blood collection, it is difficult to accurately collect a certain volume thereof, and therefore a case in which tests are performed with blood collection including errors will result in measurement values including the errors.

The method disclosed in JP2009-109196A is the measurement with a dilution factor of about 10, and in a case where the dilution factor is further increased to sufficiently secure a volume of diluted blood, there is a problem that a level of repeatability and reproducibility with respect to measurement values decreases, as same as in JP2003-161729A.

As described above, a blood analysis method in which a high level of repeatability and reproducibility is achieved with respect to measurement values in a case of using a small volume of a blood sample, is desired. An object to be solved by the present invention is to provide a blood analysis method in which a high level of repeatability and reproducibility is achieved with respect to measurement values of a blood sample of 50 µL or less, and a blood test kit which is used for the blood analysis method.

As a result of intensive studies to solve the object described above, the inventors of the present invention have found that the object described above can be solved by a configuration in which in a blood analysis method in which a collected blood sample is diluted with a diluent solution, a dilution factor is determined by using a normal value of a normal component which is homeostatically present in the blood, and a concentration of a target component in the blood sample is analyzed, a volume of the blood sample is 50 µL or less, a dilution factor of blood plasma components in the blood sample is 14 or higher, and the diluent solution which does not contain the above normal component which is homeostatically present in the blood is used as a diluent solution, and therefore have completed the present invention. That is, according to the present invention, the following inventions are provided.

(1) A blood analysis method, comprising: a step of diluting a collected blood sample with a diluent solution; a step of determining a dilution factor by using a normal value of a normal component which is homeostatically present in the blood; and a step of analyzing a concentration of a target component in the blood sample, in which a volume of the blood sample is 50 µL or less, a dilution factor of blood plasma components in the blood sample is 14 or higher, and the diluent solution is a diluent solution which does not contain the normal component which is homeostatically present in the blood.

(2) The blood analysis method according to (1), further comprising a step of recovering a blood plasma components-containing specimen from the diluted blood sample, after the step of diluting the collected blood sample with the diluent solution.

(3) The blood analysis method according to (2), in which the recovering step is a step in which a separation membrane is used.

(4) The blood analysis method according to (2) or (3), further comprising a step of transporting the blood plasma components-containing specimen, after the step of recovering the blood plasma components-containing specimen from the diluted blood sample.

(5) The blood analysis method according to any one of (1) to (4), in which the normal component which is homeostatically present in the blood is sodium ions or chloride ions.

(6) The blood analysis method according to any one of (1) to (5), in which the normal component which is homeostatically present in the blood is sodium ions or chloride ions, and at least one normal component.

(7) The blood analysis method according to (6), in which the at least one normal component is a normal component selected from total protein or albumins.

(8) The blood analysis method according to (5), in which the diluent solution is a diluent solution which does not contain sodium ions or chloride ions.

(9) The blood analysis method according to (5), in which the normal component which is homeostatically present in the blood is sodium ions.

(10) The blood analysis method according to (9), in which the diluent solution is a diluent solution which does not contain sodium ions.

(11) The blood analysis method according to any one of (1) to (10), in which the diluent solution is a buffer solution having a buffering action within a pH range of pH 6.5 to pH 8.0.

(12) The blood analysis method according to any one of (1) to (11), in which the diluent solution is a diluent solution including an amino alcohol compound selected from the group consisting of 2-amino-2-methyl-1-propanol, 2-ethylaminoethanol, N-methyl-D-glucamine, diethanolamine, and triethanolamine, and including a buffering agent selected from the group consisting of 2-[4-(2-hydroxyethyl)-1-piperazinyl]ethanesulfonic acid also called HEPES, N-tris(hydroxymethyl)methyl-2-aminoethanesulfonic acid also called TES, 3-morpholinopropanesulfonic acid also called MOPS, and N,N-bis(2-hydroxyethyl)-2-aminoethanesulfonic acid also called BES.

(13) The blood analysis method according to any one of (1) to (12), further comprising a step of verifying the analysis of a concentration of the target component by using a dilution factor obtained from a normal value of a normal component other than the above normal component.

(14) A blood test kit which is used for the blood analysis method according to any one of (1) to (13), the kit comprising: a diluent solution for diluting a blood sample; and a container for storing the diluted blood sample.

According to a blood analysis method and a blood test kit of the present invention, it is possible to perform analysis in which a high level of repeatability and reproducibility is achieved with respect to measurement values even with a small volume of a blood sample.

DESCRIPTION OF THE PREFERRED EMBODIMENTS

Hereinafter, the present invention will be described in detail.

In a case of performing a blood test, the blood is collected by inserting a blood collection needle into the vein of a subject to be tested, or the blood is collected by a method in which the skin such as a fingertip is pricked, and the blood flowing out of the skin is collected. Both methods are invasive actions that damage the skin, which is accompanied by patient's pain. Therefore, a method in which the blood is collected, in a manner of relieving patient's pain by suppressing invasiveness as much as possible to reduce the damage on the skin, and the blood is analyzed is desired from many patients. In this case, reducing the damage on the skin reduces the pain, but because a volume of blood collection becomes small, there is an adverse effect that the type of a target component that can be tested is limited. In a case of attempting to solve the above adverse effect by applying such an aspect to the test method of JP2003-161729A, by increasing a ratio of a volume of a diluent solution to a volume of blood collection, in the diluent solution by which the blood is diluted, a sufficient volume is secured for enabling tests of all of the target components to be analyzed, which is required to be tested. However, in a case where a volume of blood collection is small, a change rate in a volume of a diluent solution before and after diluting the blood becomes extremely small, and a change rate of a substance used as an internal standard substance also becomes extremely small. Therefore, quantitative errors at the time of weighing and measurement errors at the time of measurement become relatively large, and there is a possibility that the reliability of the test may deteriorate due to a deterioration of measurement accuracy, a decrease in the level of repeatability and reproducibility, and the like. Accordingly, for a test in which the level of reproducibility with respect to measurement values is high, it was necessary to secure a certain volume of a blood sample, and it was necessary to perform a blood collection method which is accompanied with subject's pain to some extent.

In JP2001-330603A, a blood volume of about 100 μL was collected, but in a case where a patient collects 100 μL of blood by himself, it is required that the damage on the skin such as a fingertip is increased, which leads to patient's pain, and there is a case of feeling strong pain depending on the person. In addition, there is a concern that hemostasis may be delayed as the damage would be deep. Furthermore, in JP2001-330603A, a dilution factor is measured using 0.9 mmol/L of magnesium ions, 4.65 mmol/L of calcium ions, and 7.5 g/100 mL of total protein, the values being a homeostatic central value in blood, which are the amount of homeostatic component. However, in a case where a volume of blood collected by a patient is small, a concentration of the homeostatic component in a diluent solution decreases, resulting in a measurement error that cannot be ignored in a case of measuring the homeostatic component. As a result, the error is also included in the measurement values of a dilution factor, and therefore the reliability of measurement deteriorates.

In the method of JP2009-122082A, with respect to 10 μL of a blood volume, which is a small volume, a certain volume thereof is accurately collected with a micropipette so as to be analyzed, but in a case where the blood is collected by a patient, there are many patients who lack experience in blood collection, and therefore it is difficult to accurately and constantly collect a certain volume thereof. In a case where the blood is collected by a patient, the blood is collected repeatedly, and therefore a large volume of the blood flows out of the skin, but a case where tests are performed with the collected blood including errors will result in measurement values including the error.

JP2009-109196A discloses a technique for improving measurement accuracy by correcting the influence of chyle through utilization of light of two wavelengths, but the measurement is performed with a dilution factor of about 10. The method of JP2009-109196A is effective for analysis in which a volume of diluted blood is 100 μL or less, but an amount of target components to be analyzed is small, and therefore, the method cannot be applied to a test to be used for a prediction and the like of a state of the organ and a lifestyle habit by obtaining information of a plurality of target components to be analyzed. In this case, in a case where a dilution factor is further increased to sufficiently secure the volume of diluted blood, the same problem occurs as in JP2003-161729A.

The present invention has been examined in consideration of the above problems. According to a blood analysis method and a blood test kit of the present invention, even in a case where a volume of blood to be collected is set to be small so as to alleviate the burden on a patient by reducing the invasiveness when collecting the blood, it is possible to realize a dilution factor by which a high level of reproducibility is achieved when a volume of a diluent solution to be analyzed with a high dilution factor is sufficiently secured, and to accurately perform analysis of a target component. The fact that it is possible to perform analysis in which a high level of repeatability and reproducibility is achieved with respect to measurement values by using a diluent solution which does not contain a normal component homeostatically present in the blood as a diluent solution to determine a dilution factor by using a normal value of the normal component in a case where a volume of blood to be collected is set to be small and a dilution factor is set to be high, is an unexpected effect which could have not been predicted from the documents of the related art.

[1] Blood Analysis Method

The blood analysis method of the present invention is a method which includes a step of diluting a collected blood sample with a diluent solution; a step of determining a dilution factor by using a normal value of a normal component which is homeostatically present in the blood; and a step of analyzing a concentration of a target component in the blood sample, and in which a volume of the blood sample is 50 μL or less, a dilution factor of blood plasma components in the blood sample is 14 or higher, and the diluent solution is a diluent solution which does not contain the normal component homeostatically present in the blood.

In the present invention, a blood sample is collected to analyze a target component in the blood sample. The blood analysis method of the present invention may be carried out by self-blood collection in which a subject collects blood by himself, or may be carried out by general blood collection in which a qualified person such as a doctor collects blood using a syringe.

As a preferred embodiment, a patient himself pricks a fingertip and the like using a blade-attached instrument such as a lancet and then collects the blood flowing out of the skin. It is preferable that the blood is collected in a manner of reducing the invasiveness so as to alleviate the burden on a patient, and when collecting the blood, it is desirable to be able to collect the blood with little pain or painlessly. In this case, it is desired that a depth and a size of the wound are small, by which a volume of blood that can be collected is very small. Accordingly, a volume of the blood sample used in the blood analysis method of the present invention (that is, a volume of the collected blood) is 50 μL or less, is preferably 40 μL or less, more preferably 30 μL or less, and further preferably 20 μL or less. A lower limit thereof is not particularly limited, but a volume is preferably 5 μL or more as a blood volume which is generally needed for performing blood analysis. In the present invention, even in a case of a small volume of a blood sample, it is possible to accurately perform analysis of a target component.

In the present invention, the collected blood sample is diluted with a diluent solution.

In a case of testing a specific organ or a specific disease such as liver function, renal function, metabolism, and the like as a blood test, analysis of a plurality of target components is generally performed at the same time in order to perform a prediction and the like of a state of the organ, a lifestyle habit, and the like by obtaining information of the plurality of target components to be measured which are specific to the organ or the disease. For example, in order to test the state of a liver, generally, a concentration of various components in the blood such as ALT (alanine transaminase), AST (aspartate aminotransferase), γ-GTP (γ-glutamyl transpeptidase), ALP (alkaline phosphatase), total bilirubin, total protein, and albumins is measured. As above, in order to measure the plurality of target components from one blood sample, a certain volume of diluted blood is required in a case of considering a possibility of measuring again. Accordingly, regarding a diluent solution for diluting the collected blood, it is required that a certain volume of the diluent solution is used. Regardless of a volume of the collected blood, as a volume of the diluent solution to be used for measuring a plurality of target components, 250 μL or more is preferable, 300 μL or more is more preferable, 350 μL or more is further preferable, and 400 μL or more is most preferable. An upper limit of a volume of the diluent solution is not particularly limited, but generally, 1000 µL or less is preferable so that a dilution ratio effective for measurement is realized.

The blood to be collected contains blood plasma components and blood cell components, but it is preferable that the diluent solution is mixed with the blood plasma components which is obtained by removing the blood cell components from the blood so as to measure a concentration of a target component in the blood plasma components. The diluent solution may be mixed therewith after separating the blood cell components from the blood in advance, or the blood cell components may be separated by using a separation membrane and the like after mixing the collected blood with the diluent solution.

In a case where the blood is left alone for a long period of time in a diluted state, for example, hemolysis occurs, which leads to the release of substances, enzymes, and the like which are present at a high concentration in the blood cells into the blood plasma or serum, by which a test result is affected. Furthermore, in a case of measuring a target component by using tone, there is a possibility that hemoglobin components affect the test. Accordingly, in the present invention, it is also possible that dilution is performed after a patient performs a step of separating the blood cells from the collected blood to recover the blood plasma. Furthermore, in the present invention, it is preferable that a blood plasma components-containing specimen is recovered from a diluted blood sample, after a step of diluting the collected blood sample with the diluent solution. A blood plasma components-containing specimen refers to a specimen which contains the blood plasma components and the diluent solution. In this case, it is possible to transport the blood plasma components-containing specimen which has been recovered in the above to a test lab, for example.

The method for recovering blood plasma by separating blood cells from the blood and the method for recovering a blood plasma components-containing specimen by separating blood cells from the diluted blood are not particularly limited. The blood can be separated into blood cell components and blood plasma components by collecting the blood in a blood collection tube containing an anticoagulant and then centrifuging the blood, or blood cell components can be separated from the blood by applying pressure on the blood components to allow the components to pass through a separation membrane such as filtration membrane, and then trapping the blood cell components with the separation membrane. In this case, an anticoagulant may be used. The step of recovering the blood plasma components is preferably a step of using the separation membrane, among the above steps. In addition, in order to ensure accuracy of measurement, it is preferable to physically separate the blood plasma from the solution portion excluding blood cell components in blood. In this case, specifically, it is possible to use a biological specimen-separation instrument having a backflow prevention means described in JP2003-270239A, and the like.

In the present invention, the blood is preferably collected with reduced invasiveness, it is important that the diluent solution of the blood is prepared from a small volume of a blood sample, and it is required that a dilution factor of blood plasma components in the blood sample is high in a case where the collected blood is diluted with the diluent solution. The dilution factor described above refers to a dilution factor of blood plasma components which is obtained by removing blood cell components from the blood components. The dilution factor of the present invention is 14 or higher, preferably 17 or higher, more preferably 21 or higher, further preferably 25 or higher, particularly preferably 30 or higher, and most preferably 40 or higher. An upper limit thereof is not particularly limited, but generally, 100 or less is preferable such that highly accurate measurement is possible. In regards to a dilution factor of the blood in a case where actual blood is diluted with a diluent solution, even with a high dilution factor of 6 or higher, a high level of repeatability and reproducibility is achieved with respect to measurement with a dilution factor in a case of performing dilution with a diluent solution, and a volume of blood collection is reduced in order to reduce the pain when a patient performs blood collection. Therefore, as a dilution factor of the blood, 8 or higher is preferable, 10 or higher is more preferable, 13 or higher is further preferable, and 18 or higher is most preferable. An upper limit thereof is not particularly limited, but generally, 50 or less is preferable such that highly accurate measurement is possible.

As above, in a method in which a target component after diluting blood plasma of which a dilution factor of blood plasma components is high, is obtained from a change rate of a concentration of a substance present in the diluent solution beforehand, in order to precisely analyze a concentration of blood plasma present in the blood before dilution, a change rate in concentration is extremely small, which leads to adverse effects that measurement error becomes high and reproducibility of measurement deteriorates. Accordingly, in the present invention, a dilution factor is determined by using a normal value of a normal component which is homeostatically present in the blood in order to improve measurement accuracy. The normal component which is homeostatically present in the blood is also called an external standard substance.

Examples of the normal component which is homeostatically present in the blood include sodium ions, chloride ions, potassium ions, magnesium ions, calcium ions, total protein, albumins, and the like. As a concentration of these normal components contained in serum and blood plasma of the blood sample, a concentration of sodium ions is 134 to 146 mmol/liter (average value: 142 mmol/liter), a concentration of chloride ions is 97 to 107 mmol/liter (average value: 102 mmol/liter), a concentration of potassium ions is 3.2 to 4.8 mmol/liter (average value: 4.0 mmol/liter), a concentration of magnesium ions is 0.75 to 1.0 mmol/liter (average value: 0.9 mmol/liter), a concentration of calcium ions is 4.2 to 5.1 mmol/liter (average value: 4.65 mmol/liter), a concentration of total protein is 6.7 to 8.3 g/100 mL (average value: 7.5 g/100 mL), and a concentration of albumins is 4.1 to 5.1 g/100 mL (average value: 4.6 g/100 mL). The present invention is for enabling measurement of a target component in a case where a volume of blood to be collected is extremely small for alleviating patient's pain. In a case where a small volume of blood is diluted with a diluent solution, it is required that a concentration of "the normal component homeostatically present in the blood", which is present in the diluent solution is accurately measured. As a dilution factor becomes high, a concentration of a component, which is originally present in the blood, in the diluent solution decreases, and depending on a dilution factor, there is a possibility that measurement error is included when measuring the concentration. Accordingly, among these "normal components which are homeostatically present in the blood", when a small volume of the blood components is diluted at a high dilution factor, it is preferable to measure the normal component present at a high concentration in a small volume of the blood so that the normal component can be detected with sufficient accuracy. In the present invention, it is preferable to use sodium ions ($Na^+$) or chloride ions ($Cl^-$) which are present at a high concentration among the components homeostatically present in the blood sample. In the present invention, it is most preferable to measure sodium ions which are present in the blood at a highest amount among the normal components homeostatically present in the blood described above. Regarding sodium ions, an average value represents a normal value (median value of the reference range), and this value is 142 mmol/liter, accounting for 90% or more of total cations in the blood plasma.

An occupancy rate of blood plasma components in the blood of a subject to be tested who is a patient is about 55% in terms of a volume ratio, but the ratio varies depending on changes in salt intake of the subject, and the like, or varies for each subject. Therefore, in the present invention, a dilution factor is determined by using a normal value of the normal component which is homeostatically present in the blood, and a concentration of a target component in a blood sample is analyzed by using the determined dilution factor. As a method for determining a dilution factor, it is possible to obtain a dilution factor by calculating a dilution factor (Y/X) of the blood plasma components in a blood sample from a measurement value (concentration X) of an external standard substance (for example, sodium ions and the like) in a diluent solution of the blood plasma, and a known concentration value (concentration Y; in a case of sodium ions, 142 mmol/liter) of the external standard substance (for example, sodium ions and the like) in the blood plasma. Using this dilution factor, a value (concentration Z) of a target component in a diluent solution of the blood plasma is measured, and by multiplying this measurement value by the dilution factor, it is possible to measure a concentration [Z×(Y/X)] of a target component to be analyzed actually contained in a blood sample.

In addition, in order to verify whether concentration analysis of a target component to be analyzed in the blood is normally performed, it is preferable that by using two or more different components which are homeostatically present in the blood as a normal component, dilution factors of blood plasma components in a blood sample are separately obtained for each, and then it is confirmed whether values thereof match. The term "match" means, with respect to two measurement values (a, b), a ratio of their differences to their average values, that is, $|a-b|/\{(a+b)/2\} \times 100$ is 20% or smaller, preferably 10% or smaller, and more preferably 5% or smaller. As a preferred embodiment, by confirming that a dilution factor obtained from a normal component homeostatically present in the blood plasma, which is other than sodium ions matches a dilution factor obtained from a concentration of sodium ions, it is possible to verify that the concentration analysis of a target component to be analyzed in the blood, which is performed using a dilution factor obtained from the measurement value of the concentration of sodium ions in a diluent solution of the blood plasma, is normally performed. Examples of the method for measuring chloride ions include the electrode method (Ion Selective Electrode: ISE) using an ion selective electrode, the enzyme method using an enzyme such as amylase, the silver nitrate titration method, and the like, and it is possible to select a method to be used appropriately depending on characteristics, sensitivity, specimen amount, and the like of a measurement specimen. In addition, examples of the normal component homeostatically present in the blood plasma, which is other than sodium ions and chloride ions are preferably selected from total protein or albumins, and more preferably selected from total protein. Examples of a method for measuring total protein include the known method such as the biuret method, the ultraviolet absorption method, the Bradford method, the Lowry method, the bicinchoninic acid (BCA) method, and the fluorescence method, and it is possible to select a method to be used appropriately depending on characteristics, sensitivity, specimen amount, and the like of a measurement specimen.

A concentration of sodium ions and a concentration of chloride ions can be measured by, for example, the flame photometric method, the glass-electrode method, the titration method, the ion selective electrode method, the enzyme activity method, and the like.

In the present invention, analyzing of a concentration of a target component in a blood sample includes determining a concentration of a target component (that is, quantitatively determining a target component), determining whether a concentration of a target component is equal to or higher than a predetermined reference value or equal to or lower than a predetermined reference value, performing qualitative analysis for detecting that a certain amount of concentration is contained, and the like, and an embodiment of analysis is not particularly limited.

In the present invention, it is possible that a normal component which is homeostatically present in the blood (hereinafter will also be referred to as homeostatic substance) is measured after dilution with a diluent solution, and a dilution factor is determined in the above-described manner to analyzed a concentration of a target component in a blood sample. The diluent solution for diluting a blood sample is a diluent solution which does not contain "a normal component homeostatically present in the blood", which is used for obtaining a dilution factor. The phrase "does not contain" in the present specification means that the solution "substantially does not contain". The phrase "substantially does not contain" means that the solution does not contain a homeostatic substance used for obtaining a dilution factor at all, or even if the homeostatic substance is contained, this means a case where an ultra-small amount of concentration is contained to the extent that does not affect measurement of a homeostatic substance in a diluent solution after diluting a blood sample. In a case where sodium ions or chloride ions are used as a homeostatic substance, a diluent solution which substantially does not contain sodium ions or chloride ions is used as a diluent solution.

In the present invention, after a blood sample collected by a patient is diluted, it is possible to transport the sample to a medical institution or a test institution so that a concentration of a target component is analyzed. There is a possibility that a long period of time is taken from blood collection to analysis, and therefore during this time, it is preferable to prevent degradation or denaturation of a target component in a diluent solution of the blood. A pH of blood is generally maintained constant at a pH of about 7.30 to 7.40 for healthy subjects. Accordingly, in order to prevent degradation or denaturation of a target component, a diluent solution is preferably a buffer solution having a buffering action within a pH range of pH 6.5 to pH 8.0, preferably pH 7.0 to pH 7.5, and further preferably pH 7.3 to pH 7.4, and the diluting solution is preferably a buffer solution containing a buffering component for suppressing variation in pH.

As the type of the buffer solution, an acetate buffer solution (Na), a phosphate buffer solution (Na), a citrate buffer solution (Na), a borate buffer solution (Na), a tartrate buffer solution (Na), a Tris (tris(hydroxymethyl) aminoethane buffer solution (Cl), a HEPES ([2-[4-(2-hydroxyethyl)-1-piperazinyl]ethanesulfonic acid]) buffer solution, a phosphate buffered saline (Na), and the like are known. Among these, as a buffer solution having a pH around 7.0 to 8.0, the phosphate buffer solution, the Tris buffer solution, and the HEPES buffer solution are representative. However, the phosphate buffer solution contains a sodium salt of phosphoric acid, the Tris buffer solution has a dissociation pKa (Ka is an acid dissociation constant) of 8.08, and thus is usually used in combination with hydrochloric acid for imparting buffering ability around pH 7.0 to pH 8.0, and a dissociation pKa of sulfonic acid of HEPES is 7.55, but in order to adjust buffer solution at constant ionic strength, a HEPES mixture of sodium oxide and sodium chloride is used. Therefore, these solutions are useful as a buffer solution having an action of maintaining pH constant, but contain sodium ions or chloride ions which are substances preferably used as an external standard substance, and thus, application thereof to the present invention is not preferable.

As the diluent solution used in the present invention, it is preferable to use a buffer solution which does not contain sodium ions or chloride ions. The diluent solution used in the present invention is preferably a diluent solution including at least an amino alcohol compound selected from the group consisting of 2-amino-2-methyl-1-propanol (AMP), 2-ethylaminoethanol, N-methyl-D-glucamine, diethanolamine, and triethanolamine, and a buffering agent selected from the group consisting of 2-[4-(2-hydroxyethyl)-1-piperazinyl]ethanesulfonic acid (pKa=7.55) also called HEPES which is a buffering agent having a pKa around 7.4, N-tris(hydroxymethyl)methyl-2-aminoethanesulfonic acid also called TES (pKa=7.50), 3-morpholinopropanesulfonic acid also called MOPS (pKa=7.20), and N,N-bis(2-hydroxyethyl)-2-aminoethanesulfonic acid also called BES (pKa=7.15), which are Good's buffer solutions (Good's buffers). Among these, a combination of 2-amino-2-methyl-1-propanol (AMP) with HEPES, TES, MOPS, or BES is preferable, and a combination of 2-amino-2-methyl-1-propanol (AMP) with HEPES is most preferable.

For preparing the buffer solution described above, an amino alcohol may be mixed with the Good's buffer solutions at a concentration ratio of 1:2 to 2:1, preferably 1:1.5 to 1.5:1, and more preferably 1:1. A concentration of the buffer solution is not limited, but a concentration of the amino alcohol or the Good's buffer solution is 0.1 to 1000 mmol/L, preferably 1 to 500 mmol/L, and more preferably 10 to 100 mmol/L.

A chelating agent, a surfactant, an antibacterial agent, a preservative, a coenzyme, a saccharide, and the like may be contained in the buffer solution in order to keep a target component to be analyzed stable. Examples of the chelating agent include ethylenediaminetetraacetic acid (EDTA), citrate, oxalate, and the like. Examples of the surfactant include a cationic surfactant, an anionic surfactant, an amphoteric surfactant, and a nonionic surfactant. Examples of the preservative include sodium azide, antibiotics, and the like. Examples of the coenzyme include pyridoxal phosphate, magnesium, zinc, and the like. Examples of the saccharide of a red blood cell-stabilizing agent include mannitol, dextrose, oligosaccharide, and the like. Particularly, by adding the antibiotics, it is possible to suppress the growth of bacteria which are partially mixed from the surface of the finger at the time of collecting blood from the finger, suppress degradation of biological components by bacteria, and stabilize the biological components.

In a case where whole blood is used for a blood sample, filtration of blood cell components in a diluted blood through a filter is required, and by setting osmotic pressure of the buffer solution equivalent to (285 mOsm/kg (mOsm/kg is an osmotic pressure that 1 kg of water of the solution has, and indicates millimoles of ions)) or higher than that of the blood, it is possible to prevent hemolysis. The osmotic pressure can be adjusted to be isotonic by measurement of a target component, salts which do not affect a normal component homeostatically present in the blood, sugars, buffering agents, and the like.

A target component to be analyzed of the present invention is not limited, and any substance contained in the blood is a target. Examples thereof include biochemical test items in blood used for clinical diagnosis, markers of various diseases such as tumor markers and hepatitis markers, and the like, and include proteins, sugars, lipids, low molecular weight compounds, and the like. In addition, regarding measurement, not only a concentration of a substance but also activity of a substance having the enzyme activity and the like is targeted. Measurement of each target component can be carried out by a known method.

[2] Blood Test Kit

A blood test kit of the present invention is a blood test kit which includes a diluent solution for diluting a blood sample and a container for storing a diluted blood sample, and is used in the blood analysis method of the present invention described above.

The material of the container is preferably a synthetic resin from the viewpoints of difficulty in breakage, sanitation, price, and the like. Examples thereof include polyethylene, polypropylene, polyvinyl chloride, polyvinylidene chloride, polystyrene, polyvinyl acetate, polyurethane, polyethylene terephthalate, polylactic acid, acrylonitrile butadiene styrene resin (ABS resin), acrylonitrile styrene resin (AS resin), acrylic resin (PMMA), polycarbonate, silicone resin, silicone rubber, and the like.

As the example of the blood test kit of the present invention, the kit can include a diluent solution for diluting a blood sample, a first storing instrument in which the diluent solution is stored, a separating instrument for separating and recovering blood plasma from the blood sample diluted with the diluent solution, a holding instrument for holding the separating instrument, a second storing instrument for storing the recovered blood plasma, a scaling instrument for keeping the blood plasma in the second storing instrument, a needle or a lancet for pricking the skin to allow blood to flow out of the skin, a strip of bandage or a sterile swab to be put on the wound (for example, nonwoven fabrics impregnated with isopropanol (70% by mass isopropanol and the like), ethanol, or the like), an instruction manual, and the like.

As a diluent solution for diluting a blood sample, it is possible to use the diluent solution described above in the present specification.

Among the first storing instrument and the second storing instrument, one instrument may be used as both the first storing instrument and the second storing instrument, or an embodiment in which instruments are provided separately may be used.

The first storing instrument and the second storing instrument are preferably made of a transparent material such that a patient or a measurer who performs measurement of a dilution factor and analysis of a target component to be analyzed can check a diluent solution in the storing instrument, by which the blood is diluted. The term "transparent" referred in the present invention may be transparent to the extent that the observer can confirm a volume of the solution therein, and is a concept including translucence and the like.

As the separating instrument for separating the blood plasma, an aspect of a separation membrane is preferable, and a filter having fine pores capable of separating blood cell components is more preferable. As the holding instrument for holding the separating instrument, an aspect of a gasket is preferable. In addition, as the sealing instrument, in a case where the storing instrument is an instrument having a tubular shape, and the like, it is possible to use a cap capable of being used as a lid for the opening, a lid having a helical groove, a rubber closure, and the like.

The present invention is capable of realizing a method in which a target component to be analyzed can be analyzed at high measurement accuracy even with a volume of blood collection of 50 µL or less, which is a small volume of blood, and is preferably a kit including an instruction manual in which information that measurement can be accurately performed even with a small volume of blood collection of 50 µL or less is described for a patient.

Figure 1:
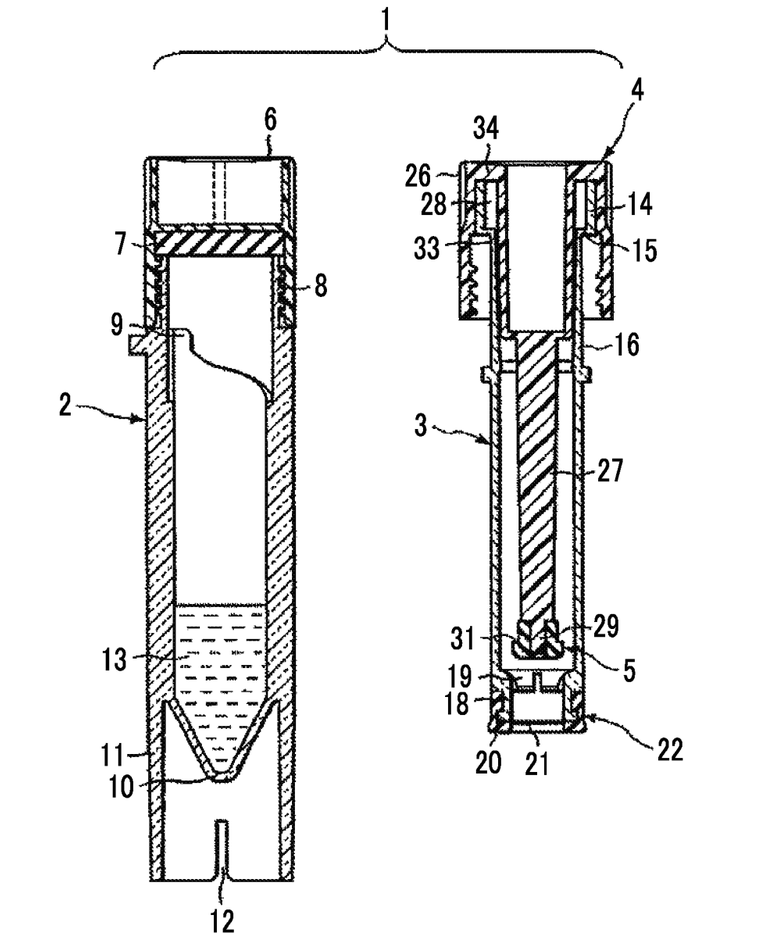
FIG. 1 illustrates an example of a configuration of a container for storing a diluted blood sample.

As a specific configuration example of the first storing instrument in which a diluent solution is stored, the separating instrument for separating and recovering blood plasma from a blood sample diluted with the diluent solution, the holding instrument for holding the separating instrument, the second storing instrument for storing the recovered blood plasma, and the sealing instrument for keeping the blood plasma in the second storing instrument, it is possible to use instruments described in FIG. 1 to FIG. 13 of JP3597827B, for example. FIG. 1 of JP3597827B is incorporated as FIG. 1 of the present application.

A blood separating instrument 1 includes a blood collection container 2 (first storing instrument in which a diluent solution is stored), a tubular body 3 capable of being to fit into the blood collection container 2 so as to be inserted (second storing instrument for storing recovered blood plasma), a cap piston 4 capable of being capped on the tubular body 3, and a sealing lid 5 (sealing instrument) provided at a lower end of the cap piston 4. Before use, an upper end opening portion of the blood collection container 2 is sealed by a cap 6 via a packing 7, as shown in FIG. 1. A container for storing a diluted blood sample of the present invention corresponds to a combination of the blood collection container 2 and the tubular body 3 in the configuration of FIG. 1. That is, the container for storing a diluted blood sample may be one or a combination of two or more thereof.

The blood collection container 2 is made of a transparent material and has a cylindrical shape. At the upper end portion thereof, a screw portion 8 is formed on the outer surface, and a locking portion 9 is protruded toward the inner surface. In addition, at a lower end portion of the blood collection container 2, a bottom portion 10 having an inverted conical shape is formed, and a cylindrical leg portion 11 is formed around the bottom portion 10. The leg portion 11 has the same outer diameter as a sample cup used at the time of an analytical test of blood, and at positions opposite to the lower end thereof, slit grooves 12 are preferably formed in a vertical direction, respectively. Furthermore, a predetermined volume, for example, 500 mm³ of a diluent solution 13 may be put in the blood collection container 2 in advance, as shown in FIG. 1.

The tubular body 3 is made of a transparent material and has a cylindrical shape, and at an upper end portion thereof, an expanded diameter section 14 is formed. The expanded diameter section 14 is connected to a main body portion 16 via a thin portion 15. A reduced diameter section 18 is formed at the lower end portion of the tubular body 3, and a protruded locking portion 19 is formed on the inner surface of the reduced diameter section 18. Furthermore, at a lower end portion of the reduced diameter section 18, an outer flange portion 20 (holding instrument) is formed, a lower end opening portion of the outer flange portion 20 is covered with a filtration membrane 21 (separating instrument), and the filtration membrane 21 allows blood plasma in the blood to pass through and prevents passage of the blood cells.

A cover 22 made of silicone rubber is attached to the outer periphery of the reduced diameter section 18 (FIG. 1).

The cap piston 4 is constituted by a substantially cylindrical knob portion 26 and a mandrel portion 27 concentric with the knob portion 26 and extending downward. At an inner upper end portion of the knob portion 26, a cylindrical space 28 into which the expanded diameter section 14 of the tubular body 3 is capable of being fitted to be inserted is formed, and the knob portion is threaded in a lower portion into which a screw can screw. The mandrel portion 27 has a lower end portion 29 formed in a pin shape, and a sealing lid 5 is detachably provided on the lower end portion 29 (refer to FIG. 1). The sealing lid 5 is made of silicone rubber.

A method for separating blood by the instruments described above is described in detail in paragraphs 0023 to 0026 and FIG. 12 and FIG. 13 of JP3597827B, the contents of which are incorporated in the present specification.

The number of various components contained in the blood test kit of the present invention is not particularly limited, and each component may be one, or there may be a plurality of, for example, 2 or more thereof.

The blood test kit of the present invention can provide the diluent solution for diluting a blood sample, the container for storing the diluted blood sample, and if desired, an arbitrary component in a manner of being stored in the storing container for storing these.

The present invention will be described by the following examples, but the present invention is not limited by the examples.

EXAMPLE

Reference Example 1

1. Preparation of Diluent Solution with which Small Volume of Blood Sample is Diluted After informed consent was obtained from a volunteer patient, 7 mL of blood collected from the vein by a syringe was obtained in a blood collection tube. From this collected blood, 80 µL, 60 µL, 40 µL, 30 µL, and 20 µL were precisely weighed 10 times respectively with a micropipette, and each was mixed with 360 µL of Diluent Solution 1 prepared as described below. The resulting mixture was allowed to pass through a filter to separate blood cell components, and therefore diluted blood plasma was obtained. Using the obtained diluted blood plasma as a specimen, each concentration of a biological component was measured by using an automatic biochemistry analyzer.

(Composition of Diluent Solution 1)

Diluent Solution 1 was prepared with the following composition. As osmotic pressure, a value measured by using OSMOATAT OM-6040 (manufactured by ARKRAY, Inc.) is shown. A unit of the osmotic pressure is an osmotic pressure that 1 kg of water of a solution has, and indicates millimoles of ions.

HEPES 50 mmol/L
2-amino-2-methyl-1-propanol (AMP) 50 mmol/L
D-Mannitol 284 mmol/L
Lithium chloride 1 mmol/L
EDTA-2K 0.8 mmol/L
PALP (pyridoxal phosphate) 0.05 mmol/L
Thiabendazole 0.0001% by mass
Amikacin sulfate 0.0003% by mass Kanamycin sulfate 0.0005% by mass
Meropenem trihydrate 0.0005% by mass
Osmotic pressure 355 mOsm/kg
pH 7.4

2. Measurement of Concentration of Sodium Ions

A concentration of sodium ions was measured with respect to each diluent solution prepared in 1. The measurement was carried out by the enzyme activity method utilizing that β-galactosidase is activated by sodium, which is that each concentration of sodium ions in the diluent solution and β-galactosidase activity are in a proportional relationship. Specifically, after diluting the dilution solution of the blood five times by using purified water not containing sodium ions, 3 µL was weighed, 52 µL of a first reagent prepared as described below was added thereto, and then heated at 37° C. for 5 minutes. To this mixture, 26 µL of a second reagent prepared as described below was added, and the change in absorbance was obtained by measuring an absorbance during 1 minute at a main wavelength of 410 nm and a complementary wavelength of 658 nm by using JCA-BM6050-type automatic biochemistry analyzer (manufactured by JEOL Ltd.). The concentration of sodium ions was measured from a calibration curve prepared in advance.

(Preparation of Reagent for Measuring Sodium Ions)

A reagent for measuring sodium ions having the following composition was prepared.

First Reagent
HEPES/LiOH (pH 8.0) 100 mmol/L
D-Mannitol 60 mmol/L
N-acetylcysteine 30 mmol/L
Magnesium sulfate 1.52 mmol/L
β-galactosidase 1.1 kU/L
TRITON (registered trademark) X-100 0.05% by mass Second Reagent
HEPES/LiOH (pH 8.0) 100 mmol/L
o-Nitrophenyl β-D-galactopyranoside 15 mmol/L A dilution factor (Y/X) of each diluent solution was obtained from a concentration of sodium ions (X) in the diluent solution obtained as above, and a normal value (Y) of a concentration of sodium ions in blood plasma of the blood. An average value of the dilution factors, and CV (coefficient of variation) (%) which is a coefficient of variation of the dilution factor of 10 specimens prepared with respect to each of the collected blood (80 µL, 60 µL, 40 µL, 30 µL, and 20 µL) were obtained. The results are shown in Table 1.

TABLE 1

| Volume of collected blood (µL) | Volume of Diluent Solution 1 (µL) | Dilution factor (average value of 10-time measurements) | CV of dilution factor (%) (10-time measurements) |
|---|---|---|---|
| 80 | 360 | 9.1 | 3.3 |
| 60 | 360 | 11.5 | 3.5 |
| 40 | 360 | 17.3 | 3.9 |
| 30 | 360 | 22.8 | 4.3 |
| 20 | 360 | 33.7 | 4.7 |

(Measurement of Lithium Ions in Diluent Solution)

Measurement of lithium ions added to the diluent solution was carried out by the chelate colorimetric method (halogenated porphyrin chelating method: perfluoro-5,10,15,20-tetraphenyl-21H,23H-porphyrin). Specifically, after diluting the dilution solution of the blood 4.5 times by using purified water not containing lithium ions, 5 µL was weighed, 55 µL of a third reagent prepared as described below was added thereto, and then heated at 37° C. for 10 minutes. With respect to this mixture, the change in absorbance was obtained by measuring an absorbance during 1 minute at a main wavelength of 545 nm and a complementary wavelength of 596 nm by using JCA-BM6050-type automatic biochemistry analyzer (manufactured by JEOL Ltd.). The concentration of lithium ions was measured from a calibration curve prepared in advance.

(Preparation of Reagent for Measuring Lithium Ions)

A reagent for measuring lithium ions having the following composition was prepared.

Third Reagent
Perfluoro-5,10,15,20-tetraphenyl-21H,23H-porphyrin 0.05% by mass
Dimethyl sulfoxide 5% by mass
Triethanolamine 2% by mass
Polyethylene glycol-t-octylphenyl ether 2% by mass
Sodium dodecyl sulfate 2% by mass A dilution factor [B/(B−A)] of each diluent solution was obtained from a concentration of lithium ions (A) in the diluent solution after a blood sample was diluted, which was obtained as above, and a concentration of lithium ions (B) in the diluent solution before diluting the blood, and therefore an average value of the dilution factors, and CV (%) which is a coefficient of variation of the dilution factor of 10 specimens prepared with respect to each of the collected blood (80 µL, 60 µL, 40 µL, 30 µL, and 20 µL) were obtained. The results are shown in Table 2.

TABLE 2

| Volume of collected blood (µL) | Volume of Diluent Solution 1 (µL) | Dilution factor (average value of 10-time measurements) | CV of dilution factor (%) (10-time measurements) |
|---|---|---|---|
| 80 | 360 | 9.2 | 2.9 |
| 60 | 360 | 11.2 | 3.9 |
| 40 | 360 | 18.5 | 6.1 |
| 30 | 360 | 21.9 | 8.7 |
| 20 | 360 | 34.2 | 11.3 |

Based on the results of Table 1 and Table 2, it can be understood that in a case of measuring the dilution factor by using a standard substance present in the diluent solution, variations of repeatability and reproducibility become high in a case where a volume of blood collection is 40 µL or less and a dilution factor is 14 or higher, but in a case where sodium ions which are homeostatic components present in the blood are used as a standard substance, a level of repeatability and reproducibility with respect to measurement values of the dilution factor is extremely high even from a case of 80 µL of a volume of blood collection and 9.1 of a dilution factor to a case of 20 µL of a volume of blood collection and 33.7 of a dilution factor.

Example 1

1. Measurement of ALT (Alanine Transaminase) and AST (Aspartate Aminotransferase)

Immediately after collecting the blood from the vein using a syringe in Reference Example 1, a lancet was used for pricking the fingertip of the same patient of the blood collection to allow blood to flow out of the skin of the fingertip, and then the patient used a sponge capable of absorbing liquid of about 20 µL to 40 µL to soak up the blood. The sponge which absorbed the blood was immersed into 360 µL of a diluent solution having the same composition as the diluent solution used in Reference Example 1 so that the blood was sufficiently extracted from the sponge to the diluent solution, blood cell components were filtered through a filter, and therefore a diluent solution having blood plasma components of the blood sample was obtained. The diluent solution was sealed and transported to another facility capable of the test. Thereafter, the diluent solution was taken out, and when a dilution factor was measured in the same manner as in the measuring method of a dilution factor using sodium ions of the blood in Reference Example 1, a dilution factor was 22.3. Based on this, it was found that a volume of blood collection was slightly less than 30 µL. When the concentrations of ALT and AST in this diluted sample were measured by using a commercially available measurement kit (TRANSAMINASE CII-TEST WAKO, manufactured by Wako Pure Chemical Industries, Ltd.), the result which almost matched the measurement values of ALT and AST which was analyzed based on the dilution factor measured by using the concentration of sodium ions of the sample of which a volume of blood collection was 30 µL in Reference Example 1, was obtained.

Example 2

A concentration of chloride ions was measured by the following method using the diluent solution from which the dilution factor of blood plasma components of the blood sample was measured using sodium ions in Example 1.

(Measurement of Concentration of Chloride Ions in Diluent Solution)

Chloride ions were measured by using an ion selective electrode (ISE). A biological specimen was allowed to flow between the ion selective electrodes selectively responding to chloride ions, and reference electrodes, and a concentration of chloride ions was calculated from the electromotive force generated between both electrodes.

The result was obtained, in which a dilution factor of the blood plasma components of the blood sample, which was obtained by measurement of a concentration of sodium ions in the diluent solution of the blood plasma, was the same value as a dilution factor obtained from the measurement value of the concentration of chloride ions of the diluent solution, and 102 mmol/L of the average value of the concentration of chloride ions homeostatically present in the blood. Based on the result, it was found that the measurement of the dilution factor obtained from the concentration of sodium ions in Example 1 was performed normally, and it was found that the verification of the measurement is possible.

EXPLANATION OF REFERENCES

1: blood separating instrument
2: blood collection container
3: tubular body
4: cap piston
5: sealing lid
6: cap
7: packing
8: screw portion
9: locking portion
10: bottom portion
11: leg portion
12: slit grooves
13: diluent solution
14: expanded diameter section
15: thin wall portion
16: main body portion
18: reduced diameter section
19: protruded locking portion
20: outer flange portion
21: filtration membrane
22: cover
26: knob portion
27: mandrel portion
28: space
29: lower end portion
31: level difference portion
33: upper end portion
34: top portion

What is claimed is:

1. A blood analysis method, comprising:
a step of diluting a collected blood sample with a diluent solution;
a step of determining a dilution factor by using a normal value of a normal component which is homeostatically present in the blood; and
a step of analyzing a concentration of a target component in the blood sample,
wherein a volume of the blood sample is 50 µL or less,
a dilution factor of blood plasma components in the blood sample is 14 or higher, and
the diluent solution is a buffer solution which does not contain the normal component which is homeostatically present in the blood, and
in the step of determining a dilution factor, a concentration of the normal component is measured by using a reagent for measuring the normal component.

2. The blood analysis method according to claim 1, further comprising:
a step of recovering a blood plasma components-containing specimen from the diluted blood sample, after the step of diluting the collected blood sample with the diluent solution.

3. The blood analysis method according to claim 2, wherein the recovering step is a step in which a separation membrane is used.

4. The blood analysis method according to claim 2, further comprising:
a step of transporting the blood plasma components-containing specimen, after the step of recovering the blood plasma components-containing specimen from the diluted blood sample.

5. The blood analysis method according to claim 1, wherein the normal component which is homeostatically present in the blood is sodium ions or chloride ions.

6. The blood analysis method according to claim 1, wherein the normal component which is homeostatically present in the blood is sodium ions or chloride ions, and at least one normal component.

7. The blood analysis method according to claim 6, wherein the at least one normal component is a normal component selected from total protein or albumins.

8. The blood analysis method according to claim 5, wherein the diluent solution is a diluent solution which does not contain sodium ions or chloride ions.

9. The blood analysis method according to claim 5, wherein the normal component which is homeostatically present in the blood is sodium ions.

10. The blood analysis method according to claim 9, wherein the diluent solution is a diluent solution which does not contain sodium ions.

11. The blood analysis method according to claim 1,
wherein the diluent solution is a buffer solution having a buffering action within a pH range of pH 6.5 to pH 8.0.

12. The blood analysis method according to claim 1,
wherein the diluent solution is a diluent solution including an amino alcohol compound selected from the group consisting of 2-amino-2-methyl-1-propanol, 2-ethylaminoethanol, N-methyl-D-glucamine, diethanolamine, and triethanolamine, and including a buffering agent selected from the group consisting of 2-[4-(2-hydroxyethyl)-1-piperazinyl]ethanesulfonic acid also called HEPES, N-tris(hydroxymethyl)methyl-2-aminoethanesulfonic acid also called TES, 3-morpholinopropanesulfonic acid also called MOPS, and N,N-bis(2-hydroxyethyl)-2-aminoethanesulfonic acid also called BES.

13. The blood analysis method according to claim 1, further comprising:
a step of verifying the analysis of a concentration of the target component by using a dilution factor obtained from a normal value of a normal component other than the above normal component.

14. A blood test kit which is used for the blood analysis method according to claim 1, the kit comprising:
a diluent solution for diluting a blood sample; and
a container for storing the diluted blood sample.

* * * * *